United States Patent [19]
Perelman et al.

[11] Patent Number: 6,091,984
[45] Date of Patent: Jul. 18, 2000

[54] MEASURING TISSUE MORPHOLOGY

[75] Inventors: Lev T. Perelman, Malden; Vadim Backman, Cambridge; Michael S. Feld, Newton; George Zonios, Cambridge; Irving Itzkan, Boston, all of Mass.; Ramasamy Manoharan, Wooster, Ohio

[73] Assignee: Massachusetts Institute of Technology, Cambridge, Mass.

[21] Appl. No.: 08/948,734

[22] Filed: Oct. 10, 1997

[51] Int. Cl.[7] .................................................. A61B 5/00
[52] U.S. Cl. ............................................................ 600/476
[58] Field of Search ................................... 600/476, 478, 600/310; 356/432

[56] References Cited

U.S. PATENT DOCUMENTS

| | | | |
|---|---|---|---|
| 3,675,768 | 7/1972 | Legorreta-Sanchez | 209/4 |
| 4,281,931 | 8/1981 | Chikama | 356/372 |
| 4,336,809 | 6/1982 | Clark | 128/665 |
| 4,515,165 | 5/1985 | Carroll | 128/664 |
| 4,655,225 | 4/1987 | Dähne et al. | 128/633 |
| 4,718,417 | 1/1988 | Kittrell et al. | 128/303.1 |
| 4,829,184 | 5/1989 | Nelson et al. | 250/358.1 |
| 4,930,516 | 6/1990 | Alfano et al. | 128/665 |
| 4,948,974 | 8/1990 | Nelson et al. | 250/358.1 |
| 5,106,387 | 4/1992 | Kittrell et al. | 606/15 |
| 5,168,162 | 12/1992 | Oong et al. | 250/339 |
| 5,243,615 | 9/1993 | Ortiz et al. | 372/34 |
| 5,284,137 | 2/1994 | Kessler et al. | 129/633 |
| 5,303,026 | 4/1994 | Strobl et al. | 356/318 |
| 5,309,907 | 5/1994 | Fang et al. | 128/633 |
| 5,313,264 | 5/1994 | Ivarsson et al. | 356/73 |
| 5,317,156 | 5/1994 | Cooper et al. | 250/345 |
| 5,345,306 | 9/1994 | Ichimura et al. | 356/346 |
| 5,369,496 | 11/1994 | Alfano et al. | 356/446 |
| 5,386,827 | 2/1995 | Chance et al. | 128/633 |
| 5,398,685 | 3/1995 | Wilk et al. | 128/653.1 |
| 5,402,778 | 4/1995 | Chance | 128/633 |
| 5,419,321 | 5/1995 | Evans | 128/633 |
| 5,421,337 | 6/1995 | Richards-Kortum et al. | 128/665 |
| 5,452,723 | 9/1995 | Wu et al. | 128/664 |
| 5,460,177 | 10/1995 | Purdy et al. | 128/633 |
| 5,491,344 | 2/1996 | Kenny et al. | 250/461.1 |
| 5,560,356 | 10/1996 | Peyman | 128/633 |
| 5,582,168 | 12/1996 | Samuels et al. | 128/633 |
| 5,582,169 | 12/1996 | Oda et al. | 128/633 |
| 5,596,987 | 1/1997 | Chance | 128/633 |
| 5,596,992 | 1/1997 | Haaland et al. | 128/664 |
| 5,625,458 | 4/1997 | Alfano et al. | 356/446 |
| 5,630,423 | 5/1997 | Wang et al. | 128/664 |
| 5,636,633 | 6/1997 | Messerschmidt et al. | 128/633 |
| 5,640,247 | 6/1997 | Tsuchiya et al. | 356/446 |
| 5,713,364 | 2/1998 | DeBaryshe et al. | 128/664 |
| 5,733,739 | 3/1998 | Zakim et al. | 435/29 |
| 5,813,987 | 9/1998 | Modell et al. | 600/473 |
| 5,919,140 | 6/1999 | Perelman et al. | 600/476 |
| 5,931,789 | 8/1999 | Alfano et al. | 600/473 |

FOREIGN PATENT DOCUMENTS

| | | |
|---|---|---|
| 92/14399 | 9/1992 | WIPO . |
| 96/29926 | 3/1996 | WIPO . |
| 96/28084 | 9/1996 | WIPO . |

OTHER PUBLICATIONS

Newton R. G., *Scattering Theory of Waves and Particles*, Second Edition Chapter 2, "Spherically Symmetric Scatterers," pp. 30–53. Chapter 3, "Limiting Cases and Approximations," pp. 54–78.

*Primary Examiner*—Marvin M. Lateef
*Assistant Examiner*—Eleni Mantis Mercader
*Attorney, Agent, or Firm*—Hamilton, Brook, Smith & Reynolds, P.C.

[57] ABSTRACT

The present invention relates to systems and methods for measuring one or more physical characteristics of material such as tissue using optical radiation. The system can use light that is scattered by a tissue layer to determine, for example, the size of nuclei in the tissue layer to aid in the characterization of the tissue. These methods can include the use of fiber optic devices to deliver and collect light from a tissue region of interest to diagnose, for example, whether the tissue is normal or precancerous.

48 Claims, 8 Drawing Sheets

MEASURING TISSUE MORPHOLOGY

GOVERNMENT SUPPORT

The invention was supported, in whole or in part, by a Grants No. P41RR02594 and CA53717 from the National Institutes For Health. The Government has certain rights in the invention.

BACKGROUND OF THE INVENTION

Methods for diagnosis of cancer at an early stage are essential for cancer prevention and therapy. Many types of cancers grow from epithelial tissues, which cover inner and outer surfaces of the human body. Many of these, for example cancer in gastrointestinal tract, progress through the stage of dysplasia. Dysplasia can be defined as neoplastic tissue which is not malignant yet, but is considered to be a precursor of malignancy. If diagnosed at this stage, most tumors are curable. In the case of gastrointestinal tumors, current methods of diagnosis are based on endoscopy. However, dysplastic tissue is frequently not endoscopically apparent. Thus, detection of dysplasia in the gastrointestinal tract and other sites often relies on sporadic sampling for this "invisible" malignant precursor. However, sporadic biopsies have a high probability of missing dysplastic changes. In some cases the biopsy procedure is impossible.

Efforts toward a substitution for standard biopsies have been made in order to provide accurate diagnosis of cancerous tissue in different organs in vivo and in real time. For this purpose, optical techniques that are non-invasive do not require tissue removal and can be performed in-vivo. Such methods provide information at the microscopic level and can thus provide for the search for very small sites which are likely to be missed by standard biopsies. While most human organs can be diagnosed by means of optical techniques, they are particularly applicable to the tissues in human body lumens, since they are easily accessible by optical probes, which can be inserted into one of the channels of a conventional endoscopic tube.

SUMMARY OF THE INVENTION

The present invention relates to the use of light to determine physical characteristics of a structured layer of material, and in particular certain qualitative information regarding the morphology of tissue structures using scattered light. Both backscattered and transillumination methods can be used, depending upon the thickness of the material and the size and distribution of the structure being measured. Examples of properties of materials that can be measured include surface roughness, parasity, cytometer measurements, or any material in which changes in the refractive index of a material correspond to changes in structures. This type of scattering spectroscopy can be differentiated from absorption spectroscopy which is unable to quantitatively measure particle morphology.

Despite extensive investigations, no reliable optical technique to diagnose dysplasia in-vivo is known. One of the difficulties resides in the fact that dysplastic changes are limited to the uppermost epithelial layer, which can be as thin as 20 $\mu$m, a one cell layer that is nearly transparent to optical radiation.

Tissue in the gastrointestinal tract, for example (other hollow organs share the same features also), is covered by a layer of cells called epithelium (from 20 $\mu$m to 300 pm thick depending on the part of the tract) supported by relatively acellular and highly vascular loose connective tissue, lamina propria, which can be up to 500 $\mu$m in thickness and contains a network of collagen and elastic fibers, and variety of white blood cell types. Beneath the lamina propria there is a muscular layer, muscularis mucosae, (up to 400 $\mu$m thick) and another layer of moderately dense connective tissue called submucosa (400–600 $\mu$m thick) containing many small blood vessels and abundant collagen and elastic fibers. The overall thickness of those layers is about 1 mm. Since a characteristic penetration depth of optical radiation into biological tissue does not usually exceed 1 mm, for a preferred embodiment it is sufficient to limit measurements of tissue by those layers.

Adenocarcinoma of the esophagus arises in metaplastic columnar epithelial cells in the esophagus, termed "Barrett's esophagus", which is a complication of long-standing gastrointestinal reflux. In this condition, the distal squamous epithelium is replaced by columnar epithelium consisting of a one cell layer which resembles that found in the intestines. Barrett's esophagus is frequently associated with dysplasia which later can progress to cancer. Trials of endoscopic surveillance of patients with Barrett's esophagus have not resulted in a reduction of esophageal cancer mortality. The most likely explanation is that dysplasia occurring in the esophagus cannot be seen with standard endoscopic imaging and sporadic biopsy sampling is necessary. This procedure can sample only about 0.3% of the tissue at risk. Thus, there is tremendous potential for sampling error.

The application of optical techniques to diagnose dysplasia in Barrett's esophagus is limited by the fact that the primary alterations in the tissue occur in the epithelium which is one cell thick (~20–30 $\mu$m) while fluorescence or reflectance spectra are mostly formed in deeper tissue layers. One of the most prominent features of a dysplastic epithelium is the presence of enlarged, hyperchromatic, and crowded nuclei. In fact, these changes in nuclei size and spatial distribution are the main markers used by a pathologist to diagnose a tissue specimen as being dysplastic. No significant changes in other tissue layers is observed. Unfortunately, epithelium does not contain strong absorbers or fluorophores, and the thickness of the epithelium is relatively small and thus negligible. These make epithelium diagnosis in Barrett's esophagus to be a difficult problem.

A preferred embodiment of the present invention relates to a system of measuring a fine structure component in backscattered light from mucosal tissue which is periodic in wavelength. This structure is ordinarily masked by a diffusive background, which must be removed to render it observable. The origin of this component is due to light which is Mie-scattered by surface epithelial cell nuclei. By analyzing the amplitude and frequency of the periodic structure, the density and size distribution of these nuclei can be extracted. These quantities are important indicators of neoplastic precancerous changes in biological tissue, and the technique can thus provide a useful tool for observing such changes in patients undergoing endoscopy.

The light that is incident on the thin layer at the tissue surface is not completely randomized. In this thin region the details of the elastic scattering process can be preserved. Mucosal tissues, which line the hollow organs of the body, generally consist of a thin surface layer of epithelial cells supported by underlying, relatively acellular connective tissue. In healthy tissues the epithelium often consists of a single, well-organized layer of cells with an endface diameter of about 10–20 $\mu$m and a height of about 25 $\mu$m. In cancerous and pre-cancerous (dysplastic) epithelium cells proliferate, the cellular layer often thickens and becomes more tightly packed, and the cell nuclei enlarge and appear darker (hyperchromatic) when stained. This may indicate increased nucleic acid density, hence increased refractive index.

A preferred embodiment of the invention utilizes a broadband light source to illuminate the region of interest in the tissue with optical radiation in the range between 350 and 700 nm. A fiber optic probe can be used to deliver and/or collect radiation from the tissue. The system can be used during endoscopy of a patient to optically survey a body lumen within the patient and thereby eliminate the need for removal of tissue for biopsy, or alternatively, can be used to aid in locating tissue suitable for biopsy.

Backscattered light is preferably collected over a small collection angle of between 2° and 12°, preferably in the range between 3° and 8°. When using an optical fiber system to collect the scattered light fibers having a numerical aperture between 0.05 and 0.22, and preferably between 0.07 and 0.1 can be used. Collection angles within this range reduce the level of background light without loss of the periodic component in the returning light.

Figure 1:
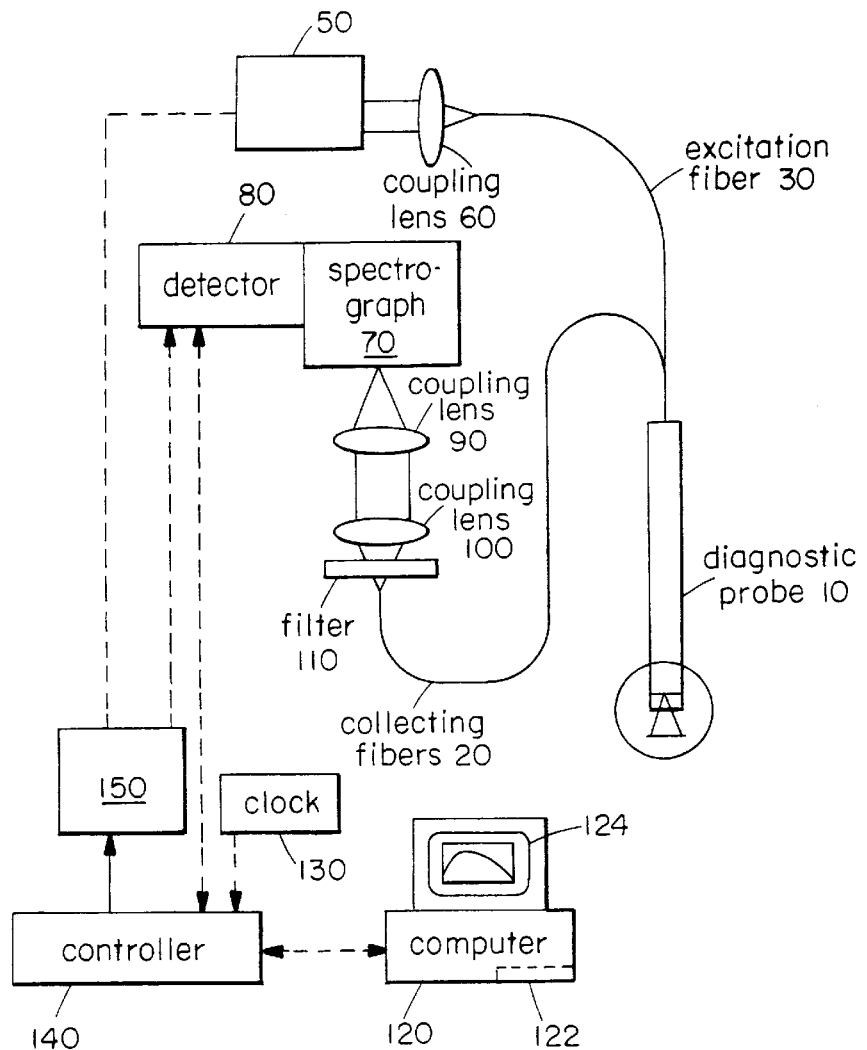
FIG. 1 is a schematic diagram of a fiber optic probe in accordance with the invention.

The foregoing and other objects, features and advantages of the invention will be apparent from the following more particular description of preferred embodiments thereof, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A preferred embodiment of the invention involves the use of a fiber optic system to deliver and collect light from a region of interest to measure one or more physical characteristics of a surface layer. Such a system is illustrated in FIG. 1. This system can include a light source 50 such as a broadband source, a fiber optic device 10 for delivery and/or collection of light from the tissue, a detector system 80 that detects the scattered light from the tissue, a computer 120 having a memory 122 that analyzes and stores the detected spectra, and a display 124 that displays the results of the measurement. A lens 60 can be used to couple light from the source 50 into the excitation fiber 30 of the probe 10. A filter 110 and lens system 90,100 can be used to efficiently couple collected light to a spectrograph 70. A controller 140 connected to the data processing system 120 can be connected to a clock and a pulser 150 that controls the light source 50.

Figure 2:
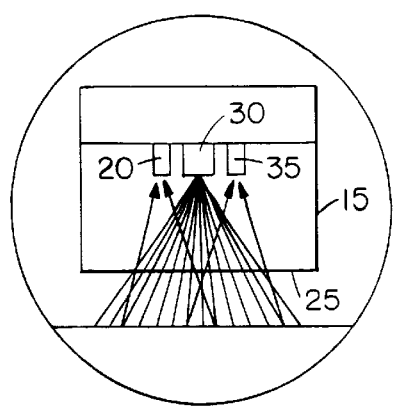
FIG. 2 is an enlarged view of the distal end of an endoscope in accordance with the invention.

The distal end 15 of the probe 10 is illustrated in FIG. 2 where the central excitation fiber 30 is surrounded by six peripheral collection fiber 20. The distal end of the device can be enclosed in an optical shield 25 such as that described in U.S. Pat. No. 5,199,431, the entire contents of which is incorporated herein by reference. Other endoscopic devices can be used such as an optical needle as described in the above referenced patent or as described in U.S. Pat. No. 5,280,788, the entire contents of which is also incorporated herein by reference.

The collection fibers 20 preferably have a numerical aperture in the range of 0.05 to 0.22 in order to provide a desired collection angle from the material being measured. This aids in reducing background that is removed from scattering spectrum without loss of the periodic component.

The collection fibers can also be replaced or supplemented by a distally mounted imaging sensor 35 such as a charged coupled device or CMOS imager. The sensor has a pixellated structure that is sensitive to the different colors contained in the scattering spectrum being recorded. Further details regarding the use of a distally mounted sensor can be found in U.S. Ser. No. 08/745,509 filed on Nov. 12, 1996, the entire contents of which is incorporated herein by reference.

The backscattered light collected with this system can be analyzed to determine certain physical characteristics of epithelial tissue. The relationship between the collected light and the physical characteristics to be determined using this light can be described as follows.

Epithelial nuclei can be represented as spheroidal Mie scatterers with a refractive index higher than that of the surrounding cytoplasm. Normal nuclei have a characteristic diameter l=4–7 μm. In contrast, dysplastic nuclei can be as large as 20 μm in size, occupying almost the entire cell volume. Thus, in the visible range, the wavelength λ<<l, and the component of light scattered by the nuclei will exhibit a periodicity with wavelength, the details of which are determined by the nuclear size distribution. The Van de Hulst approximation can be used to describe the optical scattering cross section of the nuclei:

$$\sigma_s(\lambda, l) = \frac{1}{2}\pi l^2 \left\{ 1 - \frac{\sin(2\delta/\lambda)}{\delta/\lambda} + \left(\frac{\sin(\delta/\lambda)}{\delta/\lambda}\right)^2 \right\}, \quad (1)$$

where $\delta=\pi l n_c(n-1)$, with $n_c$ the refractive index of cytoplasm and n the refractive index of the nuclei relative to that of cytoplasm.

When a beam of light is incident on an epithelial layer of tissue, a portion of this light is backscattered from the epithelial nuclei, while the remainder is transmitted to deeper tissue layers, where it undergoes multiple scattering and becomes randomized. All of the diffusive light which is not absorbed in the tissue eventually returns to the surface, passing once more through the epithelium, where it is again subject to scattering from the cell nuclei. Thus, the emerging light consists of a large diffusive background plus the component of forward scattered and backscattered light from the nuclei in the epithelial layer. For a thin slab of epithelial tissue containing nuclei with size distribution N(l) (number of nuclei per unit area (mm$^2$) and per unit interval of nuclear diameter ($\mu$m)), the approximate solution of the transport equation for the reflectance R($\lambda$) collected by an optical probe with acceptance solid angle $\Omega_c$ is given by the following expression:

$$\frac{R(\lambda)}{\overline{R}(\lambda)} = e^{-\tau(\lambda)} + 1 - \frac{e^{-\tau(\lambda)}}{I_d(\lambda,s)\Omega_c}\langle I_i(\lambda,-s^1)p(\lambda,s,-s^1)\rangle\Omega_i + \langle I_d(\lambda,s^1)p(\lambda,s,s^1)\rangle_{2\pi}\rangle\Omega_c \quad (2)$$

where $I_i((\lambda,s))$ is the intensity of the incident light delivered in solid angle $\Omega_i$, $I_d(\lambda,s)$ is the intensity of the light emerging from the underlying tissue, and $\langle I(s)\rangle\Omega = \int_\Omega I(s)ds$ for any function I(s) and solid angel $\Omega$, with s a unit vector pointing outward from the tissue surface in an arbitrary direction. The quantity $\overline{R}(\lambda) = \langle I_d(\lambda,s)\rangle\Omega_c/\langle I_i(\lambda,s)\rangle\Omega_c$ is the reflectance of the diffusive background. The optical distance $$\tau(\lambda) = \int_0^\infty \sigma_s(\lambda,l)N(l)dl$$

and scattering phase function $$p(\lambda,s,s^1) = \frac{1}{\tau}\int_0^\infty \rho(\lambda,l,s,s^1)\sigma_s(\lambda,l)N(l)dl$$

for a sphere, p($\lambda$,l,s,s$^1$) is determined by Mie theory. The first term in Eq. (2) describes the attenuation of the diffusive background, and the terms in brackets describe backscattering of the incident light and forward scattering of diffusive background by the epithelial cell nuclei, respectively.

For small $\Omega_c$ the forward scattering term in Eq. (2) can be expanded in $\tau(\lambda)$. Thus, $$\langle (I_d(\lambda,s^1)p(\lambda,s,s^1)\rangle 2\pi\rangle\Omega_c/\langle I_d(\lambda,s)\rangle\Omega_c \cong f_0 + f_1\tau/\tau_0, \text{ with}$$

$$\tau_0 = \pi/2\int_0^\infty l^2 N(l)dl.$$

It is found numerically that $f_1 \ll f_0$ and that $f_0$ and $f_1$ are approximately independent of wavelength in the range of interest ($\lambda_{min}$=360 to $\lambda_{max}$=685 nm). Similarly, for the backscattering term, $\langle (I_i(\lambda,-s^1)p(\lambda,s)\rangle\Omega_c/\langle I_d(\lambda,s)\rangle\Omega_c \cong b_0 - b_1\tau/\tau_0$. Note that in the forward scattering contribution the first order term oscillates in phase with $\tau(\lambda)$, as required by the optical theorem, whereas for the backscattering contribution it is out of phase. Thus, Eq. (2) reduces to $$\frac{R(\lambda)}{\overline{R}(\lambda)} = e^{-\tau(\lambda)} + (1-e^{-\tau(\lambda)})\left\{f_i + b_0 + (f_1-b_1)\frac{\tau(\lambda)}{\tau_0(\lambda)}\right\}, \quad (3)$$

which shows that the epithelial nuclei introduce a periodic fine structure component into the reflectance with a wavelength dependence similar to that of the corresponding scattering cross section. Its periodicity is approximately proportional to nuclear diameter, and its amplitude is a function of the size and number of nuclei in the epithelial layer. These quantities can be determined by analyzing the reflectance, R($\lambda$).

As example of the effects described by Eq. (2), elastic light scattering from normal T84 tumor human colonic cell monolayers (10 and 15 sites respectively) was measured and analyzed. The cells, approximately 15 $\mu$m long, were affixed to glass slides in buffer solution and placed on top of a BaSO$_4$ diffusing (and highly reflective) plate. The BaSO$_4$ plate was used to approximate the diffuse reflectance from underlying tissue. The diameters of the normal cell nuclei generally ranged from 5 to 7 $\mu$m and those of the tumor cells from 7 to 16 $\mu$m.

An optical fiber probe was used to deliver white light from a xenon arc flashlamp to the samples and collect the return reflectance signal, as shown in FIG. 1. The probe tip, 1 mm in diameter, consisted of a central delivery fiber surrounded by six collection fibers, all of which were covered with a 1 mm thick quartz optical shield. The fibers were 200 $\mu$m core fused silica, NA=0.22 ($\Omega_i=\Omega_c=\pi NA^2$) To eliminate specular reflection, the probe was beveled at 17° to the normal. At the proximal end the collection fibers were arranged in a line and imaged onto the input slit of a spectrograph. A diode array detector recorded the reflectance spectra from 360 to 685 nm.

Figure 3A:
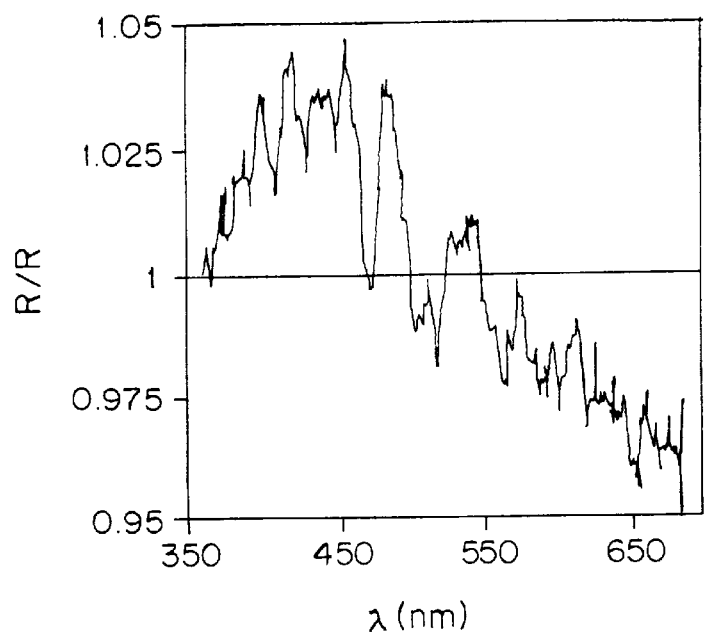
FIGS. 3A, 3B and 3C illustrate reflectance spectra from cell monolayers for normal colon cells ($\overline{R}$=0.46); T84 cells ($\overline{R}$=0.38); (c) BaSO$_4$ diffusing plate ($\overline{R}$=1.0)
Figure 3B:
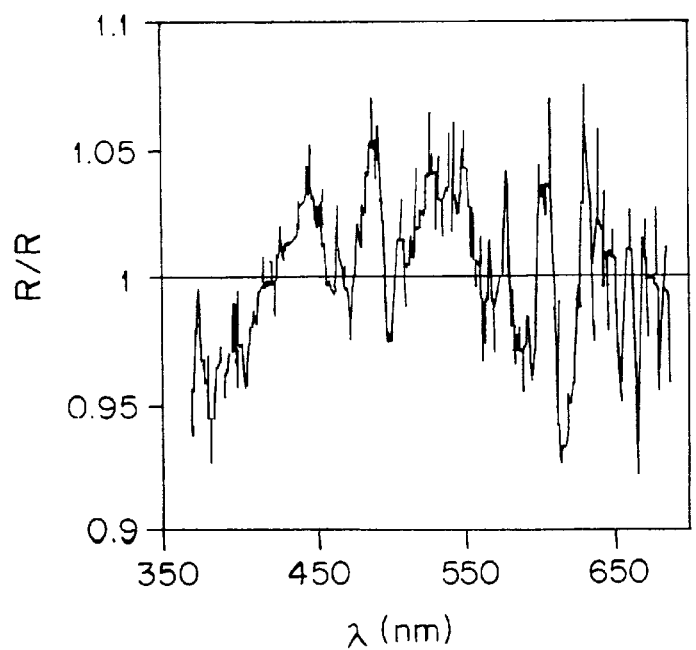
Figure 3C:
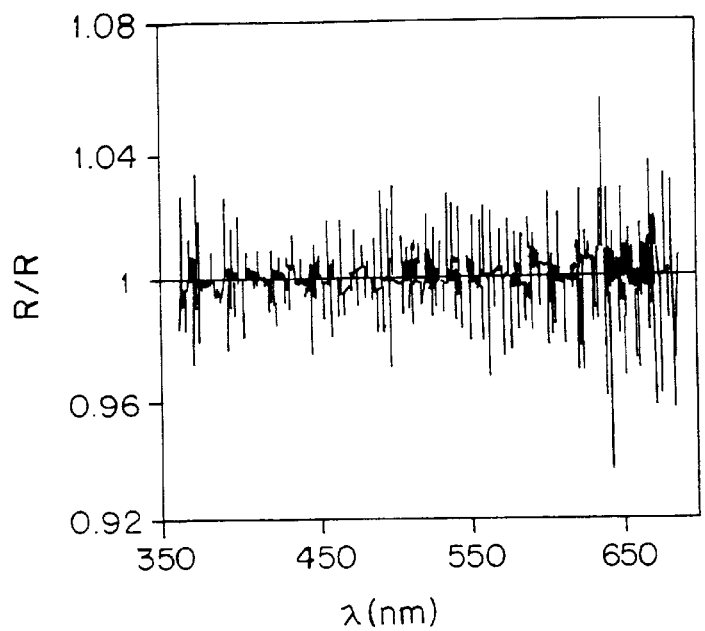

FIGS. 3A and 3B show the normalized reflectance R($\lambda$)/$\overline{R}(\lambda)$ from normal and T84 tumor cell samples, respectively. Distinct spectral features are apparent. For comparison, the reflectance spectrum from the BaSO$_4$ plate by itself is also shown in FIG. 3C. This spectrum lacks structure and shows no prominent features.

To obtain information about the nuclear size distribution from the reflectance data, Eq. (3) needs to be inverted. The nuclear size distribution, N(l), can then be obtained from the Fourier transform of the periodic component of the optical distance $\tau-\tau_0 \cong (1-R(\lambda))/q$. The parameter $q=1-b_0-f_0+2(b_1-f_1)$ is associated with forward and backward scattering, and depends on the probe geometry and the angular distribution of the incident and reflected light. In this particular example $q \approx 0.15$. By introducing the effective wavenumber $k=2\Pi n_c(n-1)/\lambda-k_0$, and $k=2\pi n_c(n-1)/\lambda_{max}$, $K=2\pi n_c(n-1)$ $$\langle \lambda_{min}^{-1}\lambda_{max}^{-1}\rangle$$

and we obtain, $$N(l) \cong \frac{2}{ql\pi^2}\left|\int_0^K \left\{\frac{R(k)}{\overline{R}(k)}-1\right\}e^{ikl}(k+k_0)dk\right|. \quad (4)$$

Figure 4:
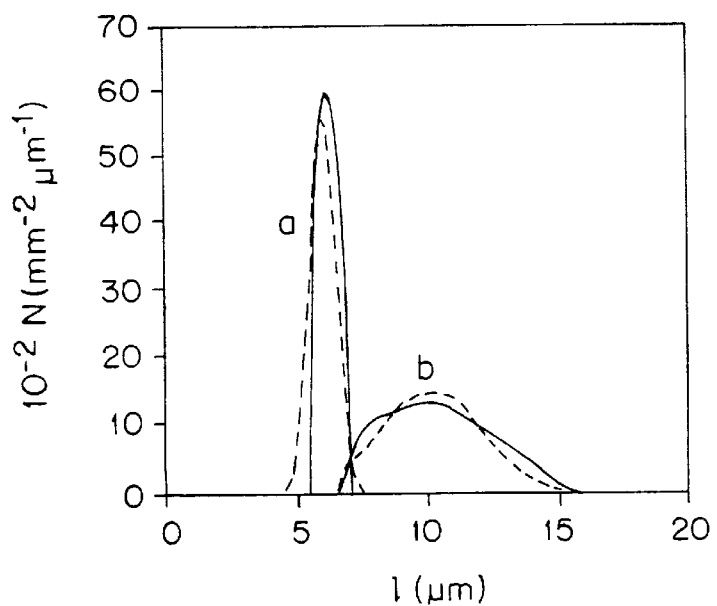
FIG. 4 illustrates nuclear size distributions from data of FIGS. 3A and 3B, respectively for normal colon cells; and T84 cells respectively. In each case, the solid line is the distribution extracted from the data, and the dashed line is the distribution measured using light microscopy.

Equation (4) was used to analyze the data. In order to remove spurious oscillations, N(l) was further processed by convolving it with a Gaussian filtering function. The solid curves in FIG. 4 show the resulting nuclear size distributions of the normal and T84 cell monolayer samples extracted from the spectra of FIGS. 3A and 3B. A nucleus-to-cytoplasm relative refractive index of n=1.06 and cytoplasm refractive index of $n_c$=1.36 were used. The dashed curves show the corresponding size distributions, measured morphometrically via light microscopy. The size distributions can be approximated by Gaussian distributions. The parameters for those are presented in Table 1. The extracted and measured distributions are in good agreement for both normal and T84 cell samples.

TABLE 1

| | Normal Cells | | Tumor T84 Cells | |
| --- | --- | --- | --- | --- |
| | Mean Diameter ($\mu$m) | Standard Deviation ($\mu$m) | Mean Diameter ($\mu$m) | Standard Deviation ($\mu$m) |
| Microscopy | ~6 | ~0.5 | 10.2 | 2.0 |
| Spectroscopy | 6.2 | 0.45 | 10.1 | 2.2 |

The periodic fine structure in diffuse reflectance of esophagus and colon mucosa of human subjects can be measured during gastroenterological endoscopy procedures. In the case of Barretts' esophagus, in which the epithelium consists of a thin monolayer of columnar cells similar to those used in the cell culture experiments, data were collected as in the cell culture studies. The optical fiber probe is inserted into the biopsy channel of the endoscope and brought into contact with the tissue surface. The methods described herein can also be used to measure structural properties of other GI tissue, tissues in the oral cavity, the cervix, the bladder, and skin.

Figure 5A:
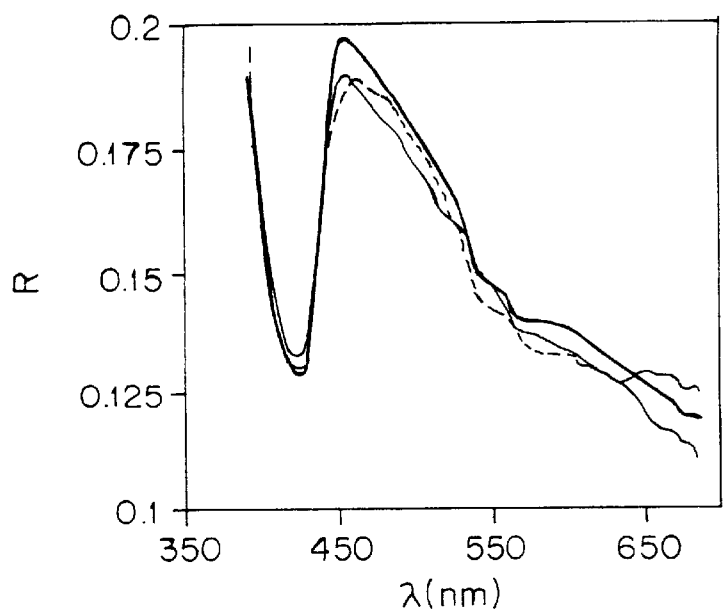
FIGS. 5A, 5B and 5C are reflectance spectra from Barretts' esophagus for diffuse reflectance from a normal site (solid line), a dysplastic site (dashed line), and the model fit (thick solid line); for corresponding fine structures; and of resulting nuclear size distributions, respectively.

The fine structure component, which is the scattering signature of the cell nuclei, is typically less than 5% of the total signal and is ordinarily masked by the background of diffusely scattered light from underlying tissue, which itself exhibits spectral features due to absorption and scattering, as shown in FIG. 5A. Its spectral features are dominated by the characteristic absorption bands of hemoglobin and collagen scattering. In order to observe the fine structure, this background must be removed. The absorption length, $\mu_a^{-1}$, ranges from 0.5 to 250 mm as the wavelength is varied, and the effective scattering length $(\mu_s')^{-1}$ ranges from 0.1 to 1 mm. Thus, both scattering and absorption have to be taken into account in subtracting or removing the background signal.

To represent the background light incident on the tissue is assumed to be exponentially attenuated, and that at any given depth, z, an amount of light proportional to the reduced scattering coefficient $\mu_s'$ is scattered back towards the surface and further exponentially attenuated. Since light attenuation depends on both scattering and absorption, the attenuation coefficient is assumed to be the sum of absorption coefficient $\mu_a$ and effective scattering coefficient $\mu_s^{(e)} = \beta \mu_s'$. The parameter $\beta$ was determined by comparison with Monte Carlo simulations and more accurate models of light transport, and was found to be $\beta \approx 0.07$. Since light only penetrates ~1 mm into the tissue, most of the diffusely scattered return light is confined to the mucosal layer.

The tissue is thereby represented as a two layer medium and neglected diffusely reflected light from the lower layer. The following approximate expression for the diffusive light from underlying tissue impinging on the epithelial cell layer is then obtained:

$$I_d(\lambda, s) = F(s)\langle I_i(\lambda, s)\rangle_{\Omega_i} \frac{1 - \exp[-(\mu_s^{(e)} + c\mu_a)L]}{1 + c(\mu_a / \mu_s^{(e)})}, \quad (5)$$

with F(s) being a Lambertian function describing the angular dependence of light emerging from mucosal layer, L a parameter representing the thickness of the mucosal layer, and L a parameter representing the thickness of the mucosal layer, and c, the concentration of hemoglobin, which we find to be the main absorber relative to that of collagen, which is responsible for light scattering. Because both oxygenated and deoxygenated hemoglobin are present, the total hemoglobin absorption is represented as $\mu_a = (1-a)\mu_a^{(Hb)} + a\mu_a^{(Hb)_2}$ with oxygen saturation parameter $a (0 \leq a \leq 1)$.

Figure 5B:
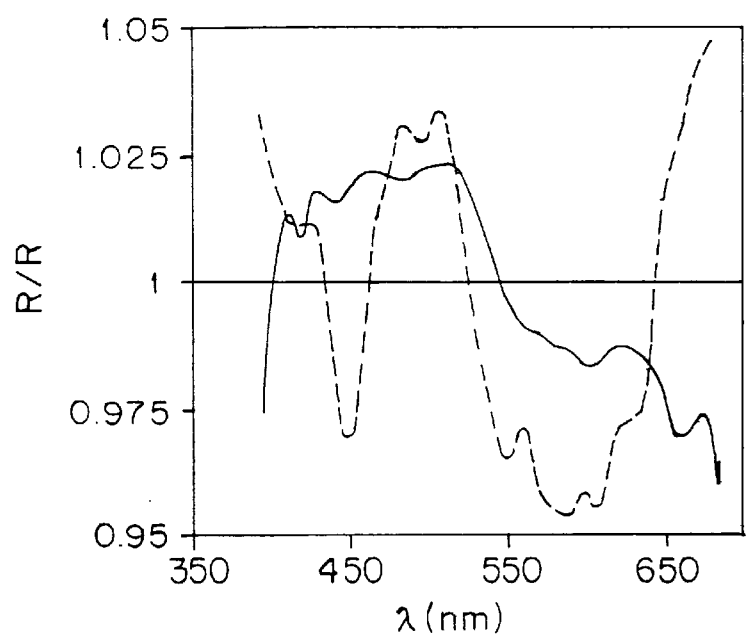
Figure 5C:
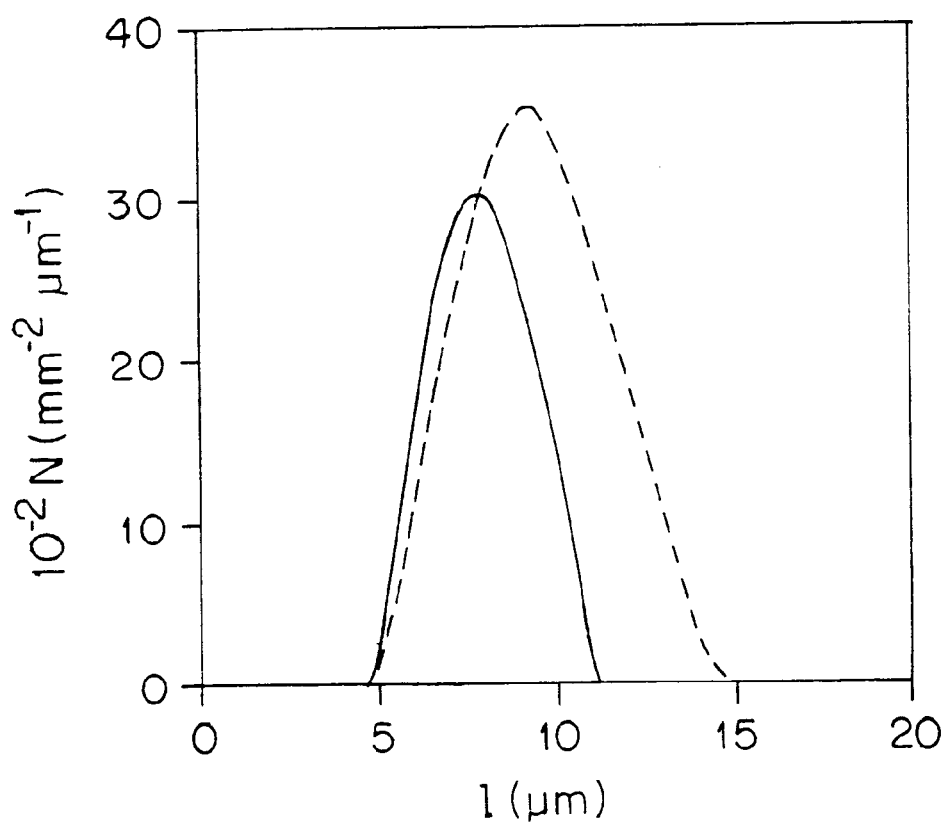

FIG. 5A shows the reflectance spectra from two Barretts' esophagus tissue sites, both independently diagnosed by standard pathological analysis to indicate (1) normal and (2) precancerous (i.e. low grade dysplasia). As can be seen, the differences in these unprocessed spectra are small. To analyze them, Eq.(5) was first fit to the broad features of the data by varying the parameters c, a and L. As seen in FIG. 5A, the resulting fits are quite accurate. After removing this diffuse background structure by calculating $R(\lambda)/\overline{R}(\lambda)$, the periodic fine structure is seen in FIG. 5B. Note that the fine structure from the dysplastic tissue site exhibits higher frequency content than that from the normal site. Equation (4) was then employed to extract the respective nuclear size distributions, yielding FIG. 5C. The difference between normal and dysplastic tissue sites is evident. The distribution of nuclei from the dysplastic site is much broader than that from the normal site and the peak diameter is shifted from ~7 $\mu$m to about ~10 $\mu$m. In addition, both the relative number of large nuclei (>10 $\mu$m) and the total number of nuclei are significantly increased.

Based on computer analysis, the uncertainty of the above method in extracting nuclear size information is estimated to be from 5% to 30%, depending on the noise level and accuracy of the model. The distributions were calculated using the same refractive index for both normal and dysplastic nuclei. This is not entirely correct, inasmuch as in stained histological sections dysplastic nuclei appear hyperchromatic, which may be indicative of an increase in refractive index. Thus, the relative number of large nuclei in the distributions measured from dysplastic sites may be slightly overestimated.

The ability to measure nuclear size distribution in vivo has valuable applications in clinical medicine. Enlarged nuclei are primary indicators of cancer, dysplasia and cell regeneration. In addition, measurement of nuclei of different size can provide information about the presence of particular cells, and can thus serve, for example, as an indicator of inflammatory response of biological tissue. This suggests that different morphology/pathology in the mucosal layer gives rise to distinct patterns of nuclear distributions.

Figure 6:
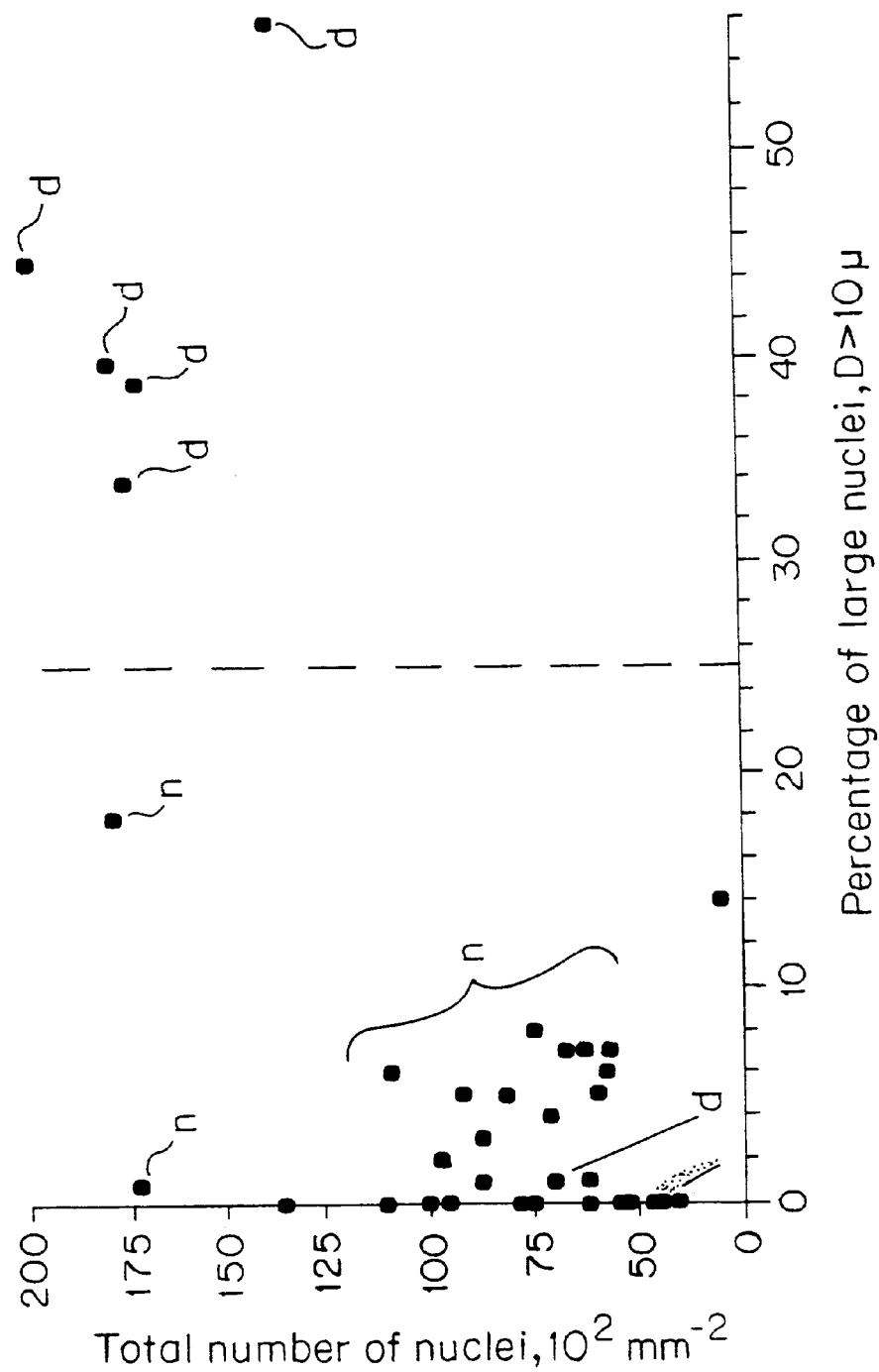
FIG. 6 graphically illustrates a comparison of samples analyzed by standard pathology and the optical methods in accordance with the invention.

The physical characteristics that have been found to be useful to differentiate between Barrett's non-dysplastic and dysplastic epithelium were the total number of nuclei and the percentage of large nuclei (l>10 $\mu$m). A comparison of pathological analysis of samples with the optical analysis thereof provided the plot (total number of nuclei vs. percentage of nuclei with a diameter large that 10 $\mu$m) in FIG. 6. From those 50 sites, the cumulative sensitivity and specificity, for this analysis were 83% and 100% respectively. The study had a positive predictive value is 100%. The points indicated by n's were either normal or inflamed and those indicated by d's were displastic. A percentage in the range of 20–30% was found to be an accurate diagnostic for this type, with 25% being used in this particular example.

Figure 7:
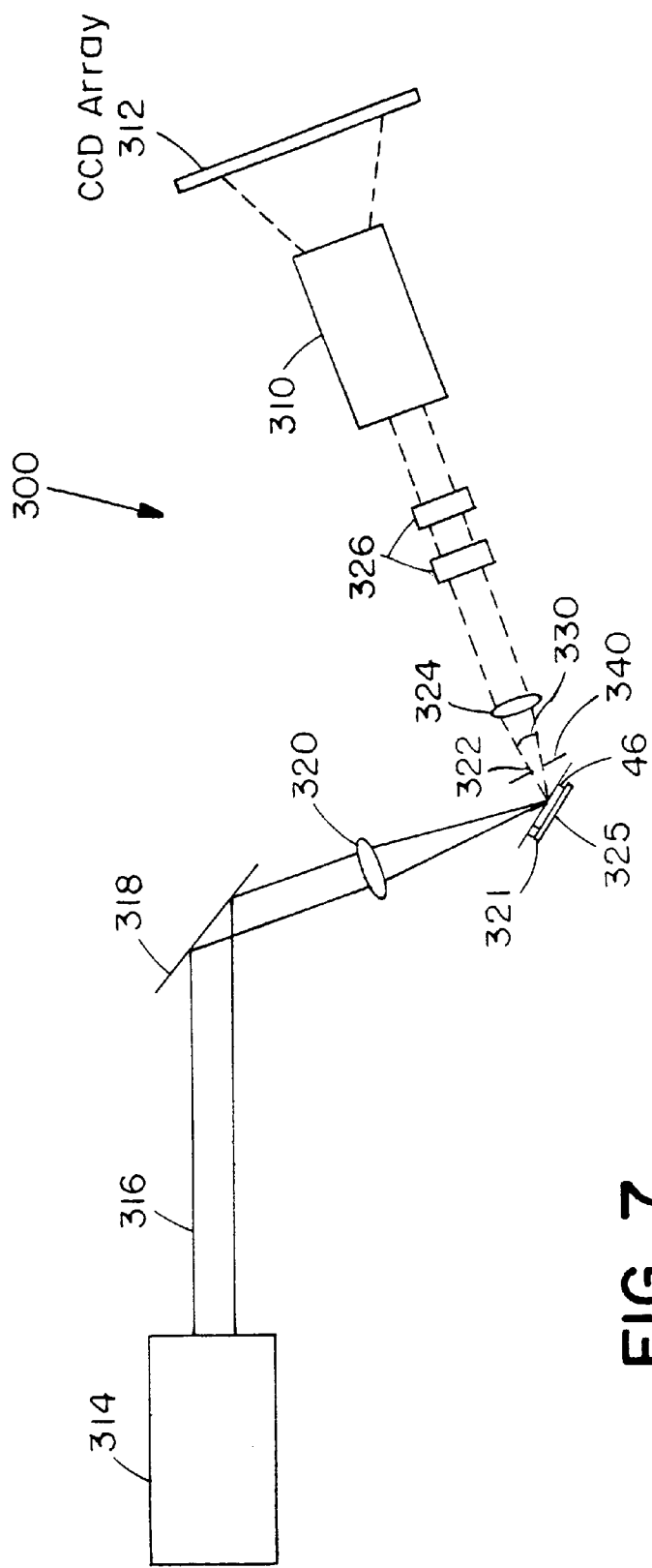
FIG. 7 is a system used for in vitro tissue analysis in accordance with the invention.

A preferred embodiment of a spectrograph system 300 employed for the collection of backscattered spectral data from excised tissue samples using a spectrograph and a charge coupled device (CCD), CMOS or other integrated solid state imaging array is illustrated in FIG. 7.

System 300 can use a broadband light source or tunable laser 314 for irradiating a sample 46. Source 314 generates a beam 316 which is directed by mirror 318 through focusing optics 320 to impinge on sample 46 mounted on a scattering substrate 325 and behind a transparent window 321. The beam was focused on the sample at an angle of incidence. The collection angle 330 can be determined by an aperture or collimator 340 and is between 2 and 12 degrees, preferably between 3 and 8 degrees.

A portion of the scattered light 322 emitted by sample 46 was collected by collecting optics 324 a small angle relative to the incident light. In another preferred embodiment the angle of incidence and collection can be along a single common axis. Collecting optics 324 collimates and F/matches the collected light for the spectrograph 310. Prior to entering the entrance slit of the spectrograph 310, the collected light was passed through a series of filters 326 which attenuated the unwanted scattered component of the collected light.

Figure 8:
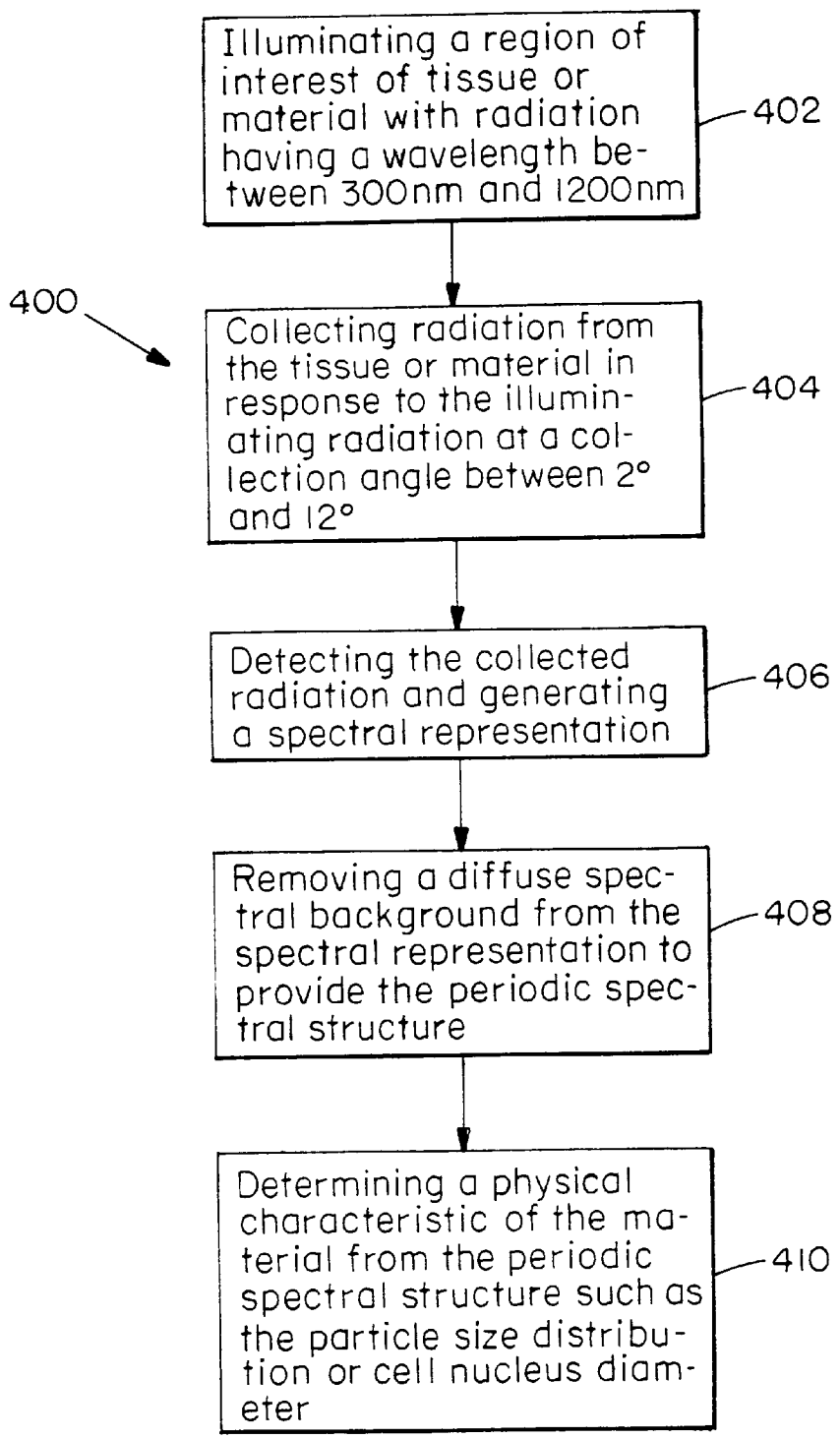
FIG. 8 is a process flow diagram illustrating a method of performing an optical diagnosis of tissue in accordance with the invention.

FIG. 8 illustrates generally a process 400 for collecting and analyzing the scattering spectrum from a material of interest such as tissue. The method can be performed both in vitro using a microscopy system or a color imaging system as shown in FIG. 7, or in vivo on a patient. The illuminating light 402 from a source can use radiation in the range of 300 nm–1200 nm, including the infrared range. After collecting 404 and detecting 406 radiation, the diffuse background 408 can be removed and the desired characteristics calculated 410. These results can be used to provide a diagnosis of the region of interest.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A method of measuring a size of a structure in a layer of tissue comprising:

directing incident radiation from a broadband light source onto a region of interest in the layer of tissue;

collecting scattered radiation from the tissue at a plurality of wavelengths;

detecting the collected scattered radiation to provide a measured spectrum as a function of wavelength; and determining a size of a structure within the tissue layer with the measured spectrum.

2. The method of claim 1 further comprising determining if the region of interest includes dysplastic tissue.

3. The method of claim 1 further comprising directing radiation onto the tissue using a fiber optic probe.

4. The method of claim 1 further comprising collecting the radiation from the tissue with a fiber optic probe.

5. The method of claim 1 further comprising determining an average nuclear size of nuclei within the region of interest.

6. The method of claim 1 further comprising measuring a diameter of a tissue nucleus within the region of interest.

7. The method of claim 1 further comprising measuring a periodic component of an intensity of radiation from the tissue as a function of wavelength.

8. The method of claim 7 further comprising determining the size of a nucleus in the tissue from the periodic component.

9. A method of optically measuring tissue comprising:

directing incident radiation onto a region of interest in tissue to be measured;

collecting scattered radiation from the tissue; and measuring a periodic component of collected scattered radiation as a function of wavelength to determine a physical characteristic of the tissue.

10. The method of claim 9 further comprising determining if the region of interest includes dysplastic tissue.

11. The method of claim 9 further comprising directing radiation onto the tissue using a fiber optic probe.

12. The method of claim 9 further comprising collecting the radiation from the tissue with a fiber optic probe.

13. The method of claim 9 further comprising determining an average nuclear size of nuclei within the region of interest.

14. The method of claim 9 further comprising measuring a diameter of a tissue nucleus within the region of interest.

15. The method of claim 9 further comprising collecting radiation with an endoscope, the endoscope having an imaging sensor at a distal end of the endoscope.

16. The method of claim 9 further comprising determining a density of nuclei in the tissue from the periodic component.

17. A method of determining a presence of dysplasia in tissue comprising:

directing incident radiation onto a region of interest in an epithelial layer of tissue;

collecting backscattered radiation from the tissue;

detecting the collected backscattered radiation with a detector;

determining a size of a structure within the epithelial layer of tissue using the detected radiation; and determining the presence of dysplasia in the region of interest of the tissue.

18. The method of claim 17 further comprising determining if the region of interest includes dysplastic tissue.

19. The method of claim 17 further comprising collecting radiation in the range of 350 nm to 700 nm.

20. The method of claim 17 further comprising collecting the radiation from the tissue with a fiber optic probe.

21. The method of claim 17 further comprising determining an average nuclear size of nuclei within the region of interest.

22. The method of claim 17 further comprising measuring a diameter of a tissue nucleus within the region of interest.

23. The method of claim 17 further comprising measuring a periodic component of an intensity of scattered radiation from the tissue as a function of wavelength.

24. The method of claim 17 further comprising determining the size of a nucleus in the tissue from the periodic component.

25. A method of optically measuring a material comprising:

directing incident radiation onto a region of interest in the material tissue to be measured;

collecting scattered radiation from the material;

detecting a scattering spectrum from the collected scattered radiation; and measuring a periodic component of collected scattered radiation as a function of wavelength to determine a physical characteristic of the material.

26. The method of claim 25 further comprising directing radiation onto the material using a fiber optic probe.

27. The method of claim 25 further comprising collecting the radiation from the material with a fiber optic probe, the probe having an optical fiber with a numerical aperture in a range of 0.05–0.25.

28. The method of claim 25 further comprising determining an average nuclear size of nuclei within the region of interest.

29. The method of claim 25 further comprising measuring a number of particles per unit area within the region of interest.

30. An apparatus for optically measuring tissue comprising:
- a radiation source that illuminates a region of interest in tissue to be measured with incident radiation;
- an optical system that collects scattered radiation from the tissue;
- a detector system that senses the collected scattered radiation; and
- a data processor that determines a periodic component of detected radiation as a function of wavelength to determine a physical characteristic of the tissue.

31. The apparatus of claim 30 further comprising a broadband light source that generates light in a range of 350–700 nm.

32. The apparatus of claim 30 further comprising a fiber optic probe that couples the source to the tissue.

33. The apparatus of claim 30 further comprising a fiber optic probe that collects the light in a collection angle between 2 and 12 degrees.

34. The apparatus of claim 33 wherein the probe is insertable in an endoscope.

35. A method of measuring a size of a structure in a layer of tissue comprising:
- directing incident radiation onto a region of interest in the layer of tissue;
- collecting scattered radiation from the tissue;
- detecting the collected scattered radiation; and
- determining an average nuclear size of nuclei within the region of interest using the detected radiation.

36. The method of claim 35 further comprising determining if the region of interest includes dysplastic tissue.

37. The method of claim 35 further comprising directing radiation onto the tissue using a fiber optic probe.

38. The method of claim 35 further comprising collecting the radiation from the tissue with a fiber optic probe.

39. The method of claim 35 further comprising measuring a diameter of a tissue nucleus within the region of interest.

40. The method of claim 35 further comprising measuring a periodic component of an intensity of radiation from the tissue as a function of wavelength.

41. The method of claim 40 further comprising determining the size of a nucleus in the tissue from the periodic component.

42. A method of measuring a size of a structure in a layer of tissue comprising:
- directing incident radiation onto a region of interest in the layer of tissue;
- collecting scattered radiation from the tissue;
- detecting the collected scattered radiation; and
- measuring a diameter of a tissue nucleus within the region of interest with the detected radiation.

43. The method of claim 42 further comprising determining if the region of interest includes dysplastic tissue.

44. The method of claim 42 further comprising directing radiation onto the tissue using a fiber optic probe.

45. The method of claim 42 further comprising collecting the radiation from the tissue with a fiber optic probe.

46. The method of claim 42 further comprising determining an average nuclear size of nuclei within the region of interest.

47. The method of claim 42 further comprising measuring a periodic component of an intensity of radiation from the tissue as a function of wavelength.

48. The method of claim 47 further comprising determining the size of a nucleus in the tissue from the periodic component.

* * * * *

UNITED STATES PATENT AND TRADEMARK OFFICE
CERTIFICATE OF CORRECTION

| | | |
|---|---|---|
| PATENT NO. | : 6,091,984 | Page 1 of 1 |
| APPLICATION NO. | : 08/948734 | |
| DATED | : July 18, 2000 | |
| INVENTOR(S) | : Perelman et al. | |

It is certified that error appears in the above-identified patent and that said Letters Patent is hereby corrected as shown below:

Col. 1, line 2 insert the following:
-- This invention was made with government support under Grant Numbers R01 CA53717 and P41-RR02594 awarded by the National Institutes of Health. The government has certain rights in the invention. --

Signed and Sealed this
Twenty-first Day of February, 2012

David J. Kappos
*Director of the United States Patent and Trademark Office*